United States Patent [19]

Markley

[11] 4,050,922

[45] Sept. 27, 1977

[54] SUBSTITUTED BENZENE-METHANOL COMPOUNDS

[75] Inventor: Lowell D. Markley, Midland, Mich.

[73] Assignee: The Dow Chemical Company, Midland, Mich.

[21] Appl. No.: 667,780

[22] Filed: Mar. 17, 1976

Related U.S. Application Data

[62] Division of Ser. No. 466,569, May 3, 1974, Pat. No. 3,972,913.

[51] Int. Cl.² .................................................. A01N 9/24
[52] U.S. Cl. .......................................... 71/106; 71/70; 71/76; 71/77; 71/122; 71/DIG. 1
[58] Field of Search ........................... 71/126, 122, 106

[56] References Cited

U.S. PATENT DOCUMENTS

| 3,375,096 | 3/1968 | Girard | 71/122 |
|---|---|---|---|
| 3,378,580 | 4/1968 | Roberts et al. | 71/126 |
| 3,509,222 | 4/1970 | Howe et al. | 71/126 |
| 3,723,091 | 3/1973 | Allais et al. | 71/122 |
| 3,819,722 | 6/1974 | Bertin et al. | 71/122 |
| 3,879,476 | 4/1975 | Deli et al. | 71/122 |

FOREIGN PATENT DOCUMENTS

| 580,712 | 8/1959 | Canada | 71/126 |
|---|---|---|---|

*Primary Examiner*—Glennon H. Hollrah
*Attorney, Agent, or Firm*—James William Ambrosius

[57] ABSTRACT

Disclosed are novel substituted benzenemethanol compounds having utility as herbicides.

37 Claims, No Drawings

SUBSTITUTED BENZENE-METHANOL COMPOUNDS

CROSS-REFERENCE TO RELATED APPLICATION

This is a division of application Ser. No. 466,569 filed May 3, 1974, now U.S. Pat. No. 3,972,913.

SUMMARY OF THE INVENTION

The present invention is directed to novel substituted benzenemethanol compounds of the following formula:

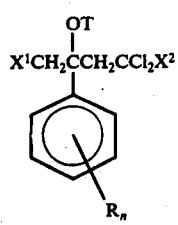
(I)

wherein $X^1$ represents bromo, chloro or iodo; $X^2$ represents hydrogen, chloro or methyl; $n$ represents an integer of 0 to 3, inclusive; R is ring-substituted in the 3-, 4- or 5-positions and each R independently represents hydrogen, trifluoromethyl, alkyl of from 1 to about 3 carbon atoms, alkoxy of from 1 to about 3 carbon atoms, bromo, chloro, fluoro or nitro, and T represents hydrogen,

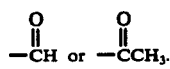

The compounds represented by the above Formula I, hereinafter referred to for convenience as "active ingredients", are useful as herbicides in the control of the growth of certain undesired plant species. Accordingly, the present invention also encompasses compositions containing one or more active ingredients as well as methods of controlling undesired vegetation. Such methods comprise applying a herbicidally-effective amount of one or more active ingredients to the locus of the undesired plant, that is, the seeds, foliage or other parts of the growing plants or soil in which the plants are growing or would grow.

DETAILED DESCRIPTION

The term "alkyl" as used herein and in the appended claims is employed to designate the radicals methyl, ethyl, propyl or isopropyl. Similarly, the term "alkoxy" is employed to mean the radicals methoxy, ethoxy, propoxy or isopropoxy. The term "herbicide" is used herein to mean an active ingredient which controls or modifies the growth of plants. By a "growth-controlling" or "herbicidally-effective" amount is meant an amount of active ingredient which causes a modifying effect and includes deviations from natural development, such as, for example, killing, retardation, defoliation, desiccation, regulation, stunting, tillering, stimulation, dwarfing and the like. The term "plants" is meant to include germinant seeds, emerging seedlings and established vegetation, including the roots and above-ground portions thereof.

The active ingredients of the present invention are crystalline solids or oils which are soluble in many organic solvents commonly employed as herbicidal carriers. The active ingredients of the above Formula I where $n$ is 0 constitute a prepared embodiment of the present invention. Active ingredients wherein $n$ is 1 constitute a further preferred embodiment. Another preferred embodiment includes active ingredients wherein $n$ is 2. In still another embodiment of the present invention, active ingredients wherein $n$ is 3 are preferred. In a further embodiment, active ingredients wherein T is hydrogen and $X^2$ is chloro are preferred. Active ingredients wherein $n$ is 1, R is chloro or bromo and is substituted in the 3-ring position are especially preferred. Another particularly preferred group of active ingredients includes those wherein $n$ is 2, R is chloro or bromo, said R groups being substituted in the 3- and 5-ring positions. A further particularly preferred group of active ingredients includes those wherein $n$ is 2, R is alkyl, said R groups being substituted in the 3- and 5-ring positions. Still a further particularly preferred group of active ingredients includes those wherein $n$ is 0 and T is hydrogen.

The active ingredients of Formula I wherein T is hydrogen can be prepared by reacting a selected substituted styrene reactant with a halogenating agent. The reaction is carried out in the presence of water and a carrier medium and can be schematically illustrated as follows:

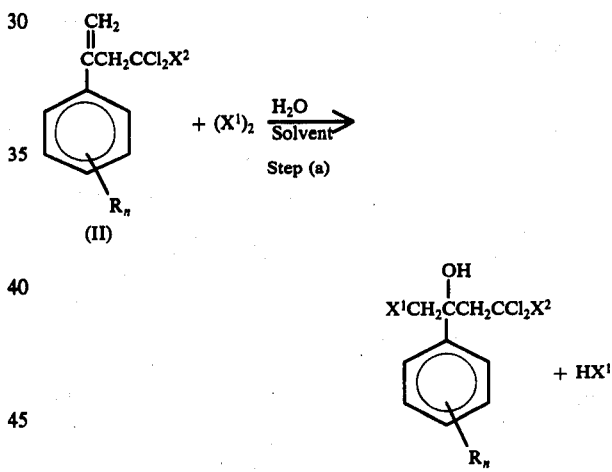

wherein $X^1$, $X^2$, $n$ and R are as previously defined.

In carrying out the reaction, the styrene reactant of Formula II is mixed with water and solvent carrier medium and the halogenating agent added thereto portionwise with stirring. Suitable carrier mediums include, for example, dioxane, isopropanol, t-butanol, glycol ethers and the like. The reaction goes forward over a wide range of temperatures, such as from about 0° to the boiling temperature of the solvent; generally, however, temperatures of from about 20° to about 40° C. are convenient and give good results. Generally, while not essential, the reactants are employed in stoichiometric proportions. Preferably, an excess amount of halogenating agent is ordinarily employed. Following the completion of the halogenating agent addition, the reaction mixture is cooled and extracted with a solvent, such as, for example, methylene chloride, chloroform, benzene or the like. The organic layer of the reaction mixture is separated and washed with water and a neutralizing agent, such as, for example, 5% sodium bicarbonate. The organic layer is subsequently dried and the solvent removed in vacuo to give the desired product as a solid or an oil. The product thus obtained can be further purified in conventional procedures, such as recrystallization, distillation or the like.

The active ingredients of the present invention wherein T is

can be obtained by carrying out Step (a) of the above reaction sequence in the presence of water and dimethylformamide. The reactants are contacted as set forth hereinabove, with the reaction mixture being maintained at temperatures of from about 0° to about −25° C. during the halogenating agent addition. The reaction mixture is usually stirred at such temperatures for periods of from about 30 to about 90 minutes following the completion of the completion of halogenating agent addition and then allowed to warm to ambient temperatures and usually stirred for another period of from about 30 to about 90 minutes. The reaction mixture is subsequently diluted with water and extracted as set forth above. The desired product is recovered from the extract and purified according to the procedures set forth above.

The active ingredients of the present invention wherein T is

are obtained by reacting a substituted styrene reactant of the above Formula II with an acetate reactant, such as, for example, silver acetate and the like, and a halogenating agent as set forth above (i.e., $(X^1)_2$) in the presence of a solvent carrier medium. A two- to three-fold excess of the acetate and halogenating agent are preferably employed. Suitable solvent carrier media include carbon tetrachloride, chloroform, benzene and the like. In carrying out the reaction, the acetate reactant is usually mixed with the solvent carrier and cooled to a temperature of from about 0° to about minus 25° C. The halogenating agent is mixed with a portion of the carrier medium and added portionwise, with stirring, to the cooled styrene reactant solution. Following the completion of the halogenating agent addition, the resulting mixture is stirred within the above temperature range for a period of ¼ to about 3 hours. A solution of the styrene reactant in a portion of the carrier medium is then added portionwise, usually dropwise, to the cooled reaction mixture. Following the completion of such addition, the reaction mixture is stirred at ambient temperatures for a period of from about 1 to about 15 hours. The reaction mixture is then filtered to remove the precipitated silver halide by-product, which is extracted with a solvent, such as methylene chloride or the like, and the extract combined with the filtrate. The mixture is then washed and the desired product removed according to the procedures set forth hereinabove.

The active ingredients of the above Formula I, wherein T is hydrogen, can also be obtained by treating the active ingredients wherein T is

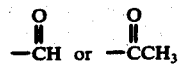

with an alkanol, such as, for example, methanol or the like in the presence of acid. The reactants are mixed together and the resulting mixture heated at reflux temperatures for a period of from about 6 to about 24 hours. Following the completion of the reaction, the mixture is cooled and the methanol removed in vacuo. The resulting residue, representing the desired product, is treated and recovered according to the typical procedures set forth hereinabove.

The following examples illustrate the present invention and the manner by which it can be practiced but, as such, are not to be construed as limitations upon the overall scope of the same.

EXAMPLE 1

A -(2,2,2-trichloroethyl)styrene (117.5 grams; 0.5 mole) was mixed with 1.0 liter of water and 1.0 liter of dioxane. Chlorine gas (42.5 grams; 0.6 mole) was vaporized into the reaction mixture over a period of about 20 minutes, with the reaction mixture temperature increasing to about 30°–35° C. Following the chlorine addition, about 1 liter of methylene chloride was added to the reaction mixture and the organic layer of the resulting mixture washed successively with 1 liter of 5% NaHCO$_3$ solution and 1 liter of water. The organic layer was then dried over sodium sulfate and the solvent removed in vacuo. Upon standing, the residue obtained yielded a crystalline material which was recrystallized from hexane to give the desired α-(chloromethyl)-α-(2,2,2-trichloroethyl)benzenemethanol product as a white crystalline solid having a melting point of 58°–60° C. The structure was confirmed by elemental and nuclear magnetic reasonance analysis.

EXAMPLE 2

α-(2,2,2-trichloroethyl)-3,5-dichlorostyrene (9.1 grams; 0.03 mole) was mixed with 100 milliliters (ml.) of dimethylformamide and 3.0 ml. of water. The resulting clear solution was cooled to about −10° C. and chlorine gas (3.2 grams; 0.04 mole) added thereto over a 10 minute period. The yellow reaction mixture was then stirred at about −10° C. for 1 hour, allowed to warm to ambient temperatures and stirred for an additional 2 hours. The reaction mixture was then diluted with 300 ml. of water. The insoluble material formed in the reaction mixture was extracted with methylene chloride (200 ml.) and the extract washed successively with water (three-200 ml. portions), 5% NaHSO$_3$ (200 ml.), water (two-100 ml. portions) and 200 ml. of a saturated sodium chloride solution. The organic layer of the mixture was then dried over sodium sulfate and reduced in vacuo. The residual oil thus obtained crystallized upon standing. The crystalline material thus obtained was recrystallized from hexane and dissolved in boiling hexane. The hexane solution was filtered, concentrated by evaporation to a volume of about 75 ml. and cooled. The resulting crystalline precipitate was recovered by filtration. As a result of such operations, the desired α-(chloromethyl)-3,5-dichloro-α-(-2,2,2-trichloroethyl)benzyl formate product was obtained as a crystalline solid having a melting point of 115°–117° C.

EXAMPLE 3

Silver acetate (17.0 grams; 0.10 mole) was mixed with 200 ml. of carbon tetrachloride and the mixture cooled in an aqueous alcohol bath to about −11° to −13° C. A solution of bromine (16.0 grams; 0.10 mole) in 100 ml. of carbon tetrachloride was added dropwise to the acetate solution while maintaining the reaction mixture temperature below about −11° C. Upon the completion of the bromine addition, the reaction mixture was stirred at temperatures below about −11° C. for about 30 minutes. Following this period, a solution of α-(2,2,2-trichloroethyl)styrene (11.2 grams; 0.05 mole) in 100 ml of carbon tetrachloride was added dropwise to the reaction mixture over a period of about 1 hour, while maintaining the reaction mixture temperature below about 5° C. The reaction mixture was warmed to ambient temperatures and stirred for a period of from about 1 to about 15 hours. Following this period the reaction mixture was filtered and the recovered silver halide precipitate extracted with methylene chloride. The extract was combined with the filtrate and the mixture washed successively with 5% NaHSO$_3$(3-100 ml. portions) and 100 ml. of water and then dried over sodium sulfate. The organic product layer was then evaporated in vacuo to obtain the desired α-(bromomethyl)-α-(2,2,2-trichloroethyl)benzyl acetate as a light yellow oil.

EXAMPLE 4

34.5 Grams of the product of Example 2 was mixed with 0.5 grams of p-toluenesulfonic acid and 400 ml. of methanol. The resulting mixture was heated under reflux conditions for a period of about 19 hours. Following the reaction period, the reaction mixture was cooled and excess methanol removed by rotary evaporation. The residual oil thus obtained was mixed with 400 ml. of methylene chloride and the resulting solution washed with 400 ml. of a 10% Na$_2$CO$_3$ solution and three-400 ml. portions of water. The organic layer was separated from the resulting mixture, dried over sodium sulfate and the methylene chloride removed by rotary evaporation. The white solid thus obtained was recrystallized from hexane. As a result of such operations, the desired α-(chloromethyl)-3,5-dichloro-α-(2,2,2-trichloroethyl)-benzenemethanol product was obtained as a white crystalline solid having a melting point of 69°-70.5° C.

Other active ingredients of the present invention are similarly prepared by employing procedures analogous to those set forth in the foregoing examples and teachings of the specification by reacting a selected substituted styrene reactant with a halogenating agent and solvent carrier. Such other active ingredients include, inter alia, the following:

α-(Bromomethyl)-α-(2,2,2-trichloroethyl)benzenemethanol as a white crystalline solid having a melting point of 62° − 68° C;

α-(Chloromethyl)-α-(2,2,2-trichloroethyl)benzyl formate, as a light yellow oil;

α-(Bromomethyl)-3,5-dimethyl-α-(2,2,2-trichloroethyl)-benzenemethanol, as a white crystalline solid having a melting point of 55° − 56.5° C.;

α-(Bromomethyl)-3-methyl-α-(2,2,2-trichloroethyl)-benzenemethanol, as a white crystalline solid having a melting point of 65° − 66.5° C.;

α-(Bromomethyl)-3-chloro-α-(2,2,2-trichloroethyl)-benzenemethanol as a light yellow oil;

α-(Bromomethyl)-3-methoxy-α-(2,2,2-trichloroethyl)-benzenemethanol, as a white crystalline solid having a melting point of 75.5° − 78° C.;

α-(Bromomethyl)-4-chloro-α-(2,2,2-trichloroethyl)-benzenemethanol, as a white crystalline solid having a melting point of 69.5° − 71° C.;

α-(Bromomethyl)-3,4-dimethyl-α-(2,2,2-trichloroethyl)-benzenemethanol, as a white crystalline solid having a melting point of 83.5° − 85° C.;

α-(Bromomethyl)-α-(2,2,2-trichloroethyl)-3-(trifluoromethyl)benzenemethanol, as a light yellow oil having a boiling point (b.p.) of 141° − 147.5° C. at 0.3 millimeters (mm) of mercury (Hg.);

α-(Bromomethyl)-4-methyl-α-(2,2,2-trichloroethyl)-benzenemethanol, as a white crystalline solid having a melting point of 85.5° − 87.5° C.;

3-Bromo-α-(Bromomethyl)-α-(2,2,2-trichloroethyl)-benzenemethanol as a light yellow oil;

α-(Bromomethyl)-α-(2,2-dichloroethyl)benzenemethanol, as a light yellow oil having a refractive index $n_D^{25} = 1.5734$ and a b.p. of 110° C. at 0.2 mm Hg.;

α-(Bromomethyl)-3,5-diethyl-α-(2,2,2-trichloroethyl)-benzenemethanol, as a yellow oil having a refractive index $n_D^{25} = 1.5595$;

α-(Bromomethyl)-α-(2,2-dichloropropyl)benzenemethanol, as a light tan crystalline solid having a melting point of 40° − 41.5° C.;

α-(Iodomethyl)-α-(2,2,2-trichloroethyl)-benzenemethanol, as a white crystalline solid having a melting point of 75° − 77.5° C.;

α-(Bromomethyl)-α-(2,2-dichloroethyl)-3,5-dimethyl-benzenemethanol, as a yellow oil having a refractive index $n_D^{25} = 1.5665$;

α-(Bromomethyl)-α-(2,2-dichloropropyl)-3,5-dimethyl-benzenemethanol, as a brown oil having a refractive index $n_D^{25} = 1.5615$;

3-Chloro-α-(chloromethyl)-α-(2,2,2-trichloroethyl)benzenemethanol, as a white solid having a melting point of 55.5° − 58.5° C.;

3-Bromo-α-(chloromethyl)-α-(2,2,2-trichloromethyl)-benzenemethanol, as a white crystalline solid having a melting point of 56° − 59° C.;

3-Bromo-α-(chloromethyl)-5-methyl-α-(2,2,2-trichloroethyl)benzenemethanol, as a light yellow oil having a refractive index $n_D^{25} = 1.5820$;

α(Bromomethyl)-3-ethyl-α-(2,2,2-trichloroethyl)benzenemethanol, as a yellow oil having a refractive index $n_D^{25} = 1.5695$;

4-Bromo-α-(bromomethyl)-3,5-dimethyl-α-(2,2,2-trichloroethyl)benzenemethanol, as a white solid having a melting point of 91° − 95° C.;

α-(Chloromethyl)-3,5-diethyl-α-(2,2,2-trichloroethyl)-benzenemethanol, as a yellow oil having a refractive index $n_D^{25} = 1.5490$;

α-(Bromomethyl)-4-chloro-3,5-dimethyl-α-(2,2,2-trichloroethyl)benzenemethanol, as a white crystalline solid having a melting point of 91° − 93° C.;

α-(Bromomethyl)-3-chloro-4-methyl-α-(2,2,2-trichloroethyl)benzenemethanol, as a white crystalline solid having a melting point of 62° − 64° C.;

α-(Bromomethyl)-3,5-bis(1-methylethyl)-α-(2,2,2-trichloroethyl)benzenemethanol, as a yellow oil having a refractive index $n_D^{25} = 1.5462$;

α-(Chloromethyl)-3-nitro-α-(2,2,2-trichloroethyl)-benzenemethanol, as a white crystalline solid having a melting point of 55.5° − 57° C.;

4-Chloro-α-(chloromethyl)-3,5-dimethyl-α-(2,2,2-trichloroethyl)benzenemethanol, as a white solid having a melting point of 67° – 69° C.;

α-(Chloromethyl)-3,5-dimethyl-α-(2,2,2-trichloroethyl)benzenemethanol, as a white solid having a melting point of 65° – 67° C.;

3,4-Dichloro-α-(chloromethyl)-α-(2,2,2-trichloroethyl)benzenemethanol, as a white solid having a melting point of 79° – 80.5° C.;

α-(Chloromethyl)-3-methoxy-α-(2,2,2-trichloroethyl)benzenemethanol, as a white solid having a melting point of 77.5° – 79.5° C.;

α-(Bromomethyl)-3,5-dichloro-α-(2,2,2-trichloroethyl)benzenemethanol, as a white crystalline solid having a melting point of 60.5° – 62.5° C.;

α-(Bromomethyl)-α-(2,2,2-trichloroethyl)benzyl acetate, as a light brown oil;

α-(Bromomethyl)-3,5-dichloro-α-(2,2,2-trichloroethyl)benzyl formate, as a white solid having a melting point of 113° – 115° C.;

α-(Chloromethyl)-3-ethyl-α-(2,2,2-trichloroethyl)benzenemethanol, as a light yellow oil having a refractive index $n_D^{25} = 1.5555$;

α-(Bromomethyl)-3-chloro-α-(2,2,2-trichloroethyl)benzyl formate, as a yellow oil;

4-Chloro-α-(chloromethyl)(2,2,2-trichloroethyl)benzenemethanol, as a white solid having a melting point of 61° – 62.5° C.;

α-(Chloromethyl)-α-(2,2,2-trichloroethyl)benzyl formate, as a yellow oil;

α-(Iodomethyl)-α-(2,2-dichloropropyl)-3,4,5-trimethylbenzyl formate;

3,5-Dibromo-α-(bromoethyl)-α-(2,2,2-trichloroethyl)benzenemethanol;

α-(Chloromethyl)-α-(2,2-dichloroethyl)-3,5-dimethoxybenzenemethanol;

3,4,5-Trichloro-α-(iodomethyl)-α-(2,2,2-trichloromethyl)benzyl formate;

3,5-Dibromo-α-(bromomethyl)-4-nitro-α-(2,2-dichloroethyl)benzenmethanol;

α-(Chloromethyl)-3-isopropoxy-5-nitro-α-(2,2-dichloropropyl)benzenemethanol;

α-(Chloromethyl)-3-fluoro-α-(2,2,2-trichloroethyl)benzenemethanol,

α-(Chloromethyl)-α-(2,2-dichloroethyl)-3,5-bis(trifluoromethyl)benzyl formate;

α(Bromoethyl)-3,5-difluoro-α(2,2,2-trichloroethyl)benzenemethanol;

α-(Bromomethyl)-4-chloro-3,5-isopropoxy-α-(2,2,2-trichloroethyl)benzenemethanol;

α(Bromomethyl)-3-chloro-5-fluoro-α-(2,2,2-trichloroethyl)benzenemethanol;

4-Chloro-α-(iodomethyl)-5-methoxy-3-methyl-α-(2,2-dichloropropyl)benzyl acetate;

α(Bromomethyl)-5-chloro-α-(2,2-dichloropropyl)-3-trifluoromethyl)benzyl formate;

α-(Chloromethyl)-3-fluoro-α-(2,2,2-trichloroethyl)benzyl formate;

α-(Chloromethyl)-5-methyl-α-(2,2,2-trichloroethyl)-3-(trifluoromethyl)benzyl formate;

3,4-Dibromo-α-(iodomethyl)-α-(2,2,2-trichloromethyl)benzenemethanol;

α-(Chloromethyl)-α-(2,2-dichloroethyl)-3,4,5-trimethoxybenzenemethanol;

α-(Bromomethyl)-3,5-dinitro-α-(2,2,2-trichloroethyl)benzyl formate;

α(Iodomethyl)-α-(2,2-dichloropropyl)-3,5-dimethyl-4-nitrobenzyl acetate;

α-(Bromoethyl)-3-fluoro-α-(2,2,2-trichloroethyl)benzyl acetate;

α-(Chloromethyl)-3,4-dinitro-α-(2,2,2-trichloroethyl)benzyl formate;

α-(Chloromethyl)-α-(2,2-dichloroethyl)-3-chloro-5-nitro-4-(trifluoromethyl)benzenemethanol;

α-(Chloromethyl)-α-(2,2-dichloroethyl)-3,4,5-trifluorobenzenemethanol;

3-Chloro-α-(iodomethyl)-3-chloro-α-(2,2-dichloropropyl)-4-methyl-5-(trifluoromethyl)benzyl formate;

α-(Chloromethyl)-3-isopropoxy-α-(2,2,2-trichloroethyl)benzyl acetate;

α-(Chloromethyl)-3-isopropyl-α-(2,2,2-trichloroethyl)benzenemethanol;

α-(Bromomethyl)-α-(2,2-dichloroethyl)-3,4-dimethylbenzyl formate;

α-(Iodomethyl)-α-(2,2-dichloropropyl)-3,4-bis(trifluoromethyl)benzenemethanol;

α-(Bromomethyl)-5-chloro-3,4-dimethyl-α-(2,2,2-trichloroethyl)benzyl formate;

α-(Chloromethyl)-3,5-dichloro-α-(2,2,2-trichloroethyl)benzyl acetate;

α-(Bromomethyl)-3,5-dimethyl-α-(2,2,2-trichloroethyl)benzyl acetate;

α-(Iodomethyl)-3,4,5-trichloro-α-(2,2,2-trichloroethyl)benzyl acetate; and

α-(Chloromethyl)-3,5-bis(trifluoromethyl)-α-(2,2,2-trichloroethyl)benzyl acetate.

The compounds of the present invention have been found to be suitable for use in methods for the pre- and post-emergent control of weeds or other unwanted vegetation. Certain of the active ingredients of the present invention have been found to be active against undesired vegetation in the presence of desired crop plants while giving little or no herbicidal action on the crop plants. For all such uses, unmodified active ingredients of the present invention can be employed. However, the present invention embraces the use of a herbicidally-effective amount of the active ingredients in composition form with an inert material known in the art as an adjuvant or carrier in solid or liquid form. Thus, for example, an active ingredient can be dispersed on a finely divided solid and employed therein as a dust. Also, the active ingredients, as liquid concentrates or solid compositions comprising one or more of the active ingredients, can be dispersed in water, typically with the aid of a wetting agent, and the resulting aqueous dispersion employed as a spray. In other procedures, the active ingredient can be employed as a constituent of organic liquid compositions, oil-in-water and water-in-oil emulsions, or water dispersions, with or without the addition of wetting, dispersing, or emulsifying agents.

Suitable adjuvants of the foregoing type are well known to those skilled in the art. The methods of applying the solid or liquid herbicidal formulations similarly are well known to the skilled artisan.

As organic solvents used as extending agents there can be employed hydrocarbons, e.g. benzene, toluene, xylene, kerosene, diesel fuel, fuel oil, and petroleum naphtha, ketones such as acetone, methyl ethyl ketone and cyclohexanone, chlorinated hydrocarbons such as carbon tetrachloride, chloroform trichloroethylene, and perchloroethylene, esters such as ethyl acetate, amyl acetate and butyl acetate, ethers, e.g., ethylene glycol monomethyl ether and diethylene glycol monomethyl ether, alcohols, e.g., methanol, ethanol, isopropanol, amyl alcohol, ethylene glycol, propylene glycol, butyl Carbitol acetate and glycerine. Mixtures of water and organic solvents, either as solutions or emulsions, can be employed.

The active ingredients can also be applied as aerosols, e.g., by dispersing them by means of a compressed gas such as dichlorodifluoromethane or trichlorofluoromethane and other Freons and Genetrons, for example.

The active ingredients of the present invention can also be applied with solid adjuvants or carriers such as talc, pyrophyllite, synthetic fine silica, attapulgus clay, kieselguhr, chalk, diatomaceous earth, lime, calcium carbonate, bentonite, fuller's earth, cottonseed hulls, wheat flour, soybean flour, pumice, tripoli, wood flour, walnut shell flour, redwood flour and lignin.

As stated, it is frequently desirable to incorporate a surface active agent in the compositions of the present invention. Such surface active or wetting agents are advantageously employed in both the solid and liquid compositions. The surface active agent can be anionic, cationic or nonionic in character.

Typical classes of surface active agents include alkyl sulfonate salts, alkylaryl sulfonate salts, alkylaryl polyether alcohols, fatty acid esters of polyhydric alcohols and the alkylene oxide addition products of such esters, and addition products of long chain mercaptans and alkylene oxides. Typical examples of such surface active agents include the sodium alkylbenzene sulfonates having 10 to 18 carbon atoms in the alkyl group, alkylphenol ethylene oxide condensation products, e.g., p-isooctylphenol condensed with 10 ethylene oxide units, soaps, e.g., sodium stearate and potassium oleate, sodium salt of propylnaphthalene sulfonic acid, di(2-ethylhexyl)-ester of sodium sulfosuccinic acid, sodium lauryl sulfate, sodium decane sulfonate, sodium salt of the sulfonated monoglyceride of coconut fatty acids, sorbitan sesquioleate, lauryl trimethyl ammonium chloride, octadecyl trimethyl ammonium chloride, polyethylene glycol lauryl ether, polyethylene glycol esters of fatty acids and rosin acids, e.g., Ethofat 7 and 13, sodium N-methyl-N-oleyl taurate, Turkey Red Oil, sodium dibutyl naphthalene sulfonate, sodium lignin sulfonate, polyethylene glycol stearate, sodium dodecylbenzene sulfonate, tertiary dodecyl polyethylene glycol thioether (nonionic 218), long chain ethylene oxide-propylene oxide condensation products, e.g., Pluronic 61 (molecular weight 1000), polyethylene glycol ester of tall oil acids, sodium octyl phenoxyethoxyethyl sulfate, tris(polyoxyethylene)sorbitan monostearate (Tween 60), and sodium dihexyl sulfosuccinate.

The concentration of the active ingredients in solid or liquid compositions generally is from about 0.003 to about 95 percent by weight or more. Concentrations of from about 0.003 to about 50 weight percent are often employed. In compositions to be employed as concentrates, the active ingredient can be present in a concentration of from about 5 to about 98 weight percent. The active ingredient compositions can also contain other compatible additaments, for example, phytotoxicants, plant growth regulants, pesticides and the like and can be formulated with solid particulate fertilizer carriers such as ammonium nitrate, urea and the like.

The present compositions can be applied by the use of power-dusters, boom and hand sprayers, spray-dusters, by addition to irrigation water, and by other conventional means. The compositions can also be applied from airplanes as a dust or a spray since certain of the active ingredients are effective at low application rates.

The exact rate to be applied is dependent not only upon the specific active ingredient being employed, but also upon the particular plant species to be modified and the stage of growth thereof as well as the part of the plant to be contacted with the toxic active ingredient. Thus, it is to be understood that all of the active ingredients of the invention and compositions containing the same may not be equally effective at similar concentrations or against the same plant species. In non-selective pre-emergence and foliage treatments, the active ingredients of this invention are usually applied at an approximate rate of from about 1 to about 25 lbs. per acre, but lower or higher rates may be appropriate in some cases. In selective pre- and post-emergence operations, a dosage of from about 0.13 to about 2.0 pounds per acre is usually employed but higher dosages may be necessary in some instances. In view of the foregoing and following disclosures, one skilled in the art can readily determine the optimum rate to be applied in any particular case.

So as to illustrate the general and selective herbicidal properties of the active ingredients of the present invention, a group of controlled greenhouse experiments is described below.

EXAMPLE 5

Various species of plants were planted in beds of good agricultural soil in a greenhouse. After the plants had emerged and grown to a height of about 2–6 inches, certain of the plants were sprayed with a given volume of a solution containing 4000 parts per million of the candidate active ingredient, prepared by mixing the selected active ingredient and emulsifier or dispersant with water. Sufficient volumes of the solutions were applied to provide approximately 10.0 pounds of active ingredient per acre. Other plants were left untreated to serve as controls.

In representative operations employing the above procedures, each of the α-(chloromethyl)-α-(2,2,2-trichloroethyl)benzenemethanol (Compound A), α-(chloromethyl)--3,5-dichloro-α-(2,2,2-trichloroethyl)benzenemethanol (Compound B), α-(bromomethyl)-3-methyl-α-(2,2,2-trichloroethyl)benzenemethanol (Compound C), α-(bromomethyl)-3-chloro-α(2,2,2-trichloroethyl)benzenemethanol (Compound D), α-(bromomethyl)-3-methoxy-α-(2,2,2-trichloroethyl)benzenemethanol (Compound E), 3-bromo-α-(bromomethyl)-α(2,2,2-trichloroethyl)benzenemethanol (Compound F), 3-bromo-α-(chloromethyl)-α-(2,2,2-trichloroethyl)benzenemethanol (Compound G), α-(bromomethyl)-4-chloro-3,5-dimethyl-α-(2,2,2-trichloroethyl) benzenemethanol (Compound H), α-(chloromethyl)-3-nitro-α-(2,2,2-trichloroethyl)benzenemethanol (Compound I), 3,4-dichloro-α-(chloromethyl)-α-(2,2,2-trichloroethyl)benzenemethanol (Compound J, and α-(chloromethyl)-3-ethyl-α-(2,2,2-trichloroethyl)benzenemethanol (Compound K) test ingredients was found to give substantial to complete (e.g., from about 70 to about 100%) control of the growth of crabgrass and barnyard grass at an application rate of about 10 pounds per acre. In further of such representative operations, each of the α-(bromomethyl)-α-(2,2,2-trichloroethyl)benzenemethanol (Compound L), α-(bromomethyl)-3,5-dimethyl-α-(2,2,2-trichloroethyl)benzenemethanol (Compound M), α-(bromomethyl)-4-chloro-α-(2,2,2-trichloroethyl)benzenemethanol (Compound N), α-(bromomethyl)-α-(2,2-dichloropropyl)benzenemethanol (Compound O), α-(bromomethyl)-α-(2,2-dichloroethyl)-3,5-dimethylbenzenemethanol (Compound P), α-(bromomethyl)-α-(2,2-dichloropropyl)-3,5-dimethylbenzenemethanol (Compound Q), 3-chloro-α-(chloromethyl)-α-(2,2,2-trichloroethyl)-benzenemethanol (Compound R), 3-bromo-α-(chloromethyl)-5-methyl-α-(2,2,2-trichloroethyl)benzenemethanol (Compound S), α-(bromomethyl)-3-ethyl-α-(2,2,2-trichloroethyl)benzenemethanol (Compound T), 4-bromo-α(bromomethyl)-3,5-dimethyl-α-(2,2,2-trichloroethyl)-benzenemethanol, (Compound U) and 4-chloro-α-(chloromethyl)-3,5-dimethyl-α-(2,2,2-trichloroethyl)-benzenemethanol (Compound V) test ingredients was found to give substantial to complete control (e.g., 70 – 100% control) of the growth of barnyard grass, crabgrass and/or Johnson grass at an application rate of about 10 pounds per acre.

In additional representative post-emergence operations, each of α-(chloromethyl)3,5-dichloro-α-(2,2,2-trichloroethyl)benzylformate (Compound W), α-(chloromethyl)-3,5-dimethyl-α-(2,2,2-trichloroethyl)-benzenemethanol (Compound X), α-(bromomethyl)-3,5-dichloro-α-(2,2,2-trichloroethyl) benzenemethanol (Compound Y), α-(bromomethyl)-3,5-dichloro-α(2,2,2-trichloroethyl)benzyl formate (Compound Z) and α-(bromomethyl)-3-chloro-α-(2,2,2-trichloroethyl)benzyl formate test ingredients was found to give substantial to complete control of yellow foxtail at an application rate of about 10 pounds per acre. Each of these test ingredients was further found to give excellent control of yellow foxtail at very low application rates of from between about 0.16 to about 1.25 pounds with little or no phytotoxic effect to one or more of certain desired crop plants, such as, for example, corn, soybeans, sugar beets or cotton.

Certain of the above and other active ingredients of the present invention are also found to be active in general post-emergent operations against one or more of the above weed species as well as one or more of other plant species, such as, for example, wild oats, pigweeds and German millet at various application rates. Many of the active ingredients of the present invention are found to be active against certain undesired plant species while being substantially non-phytotoxic to certain desired crop plants at various application rates. Illustratively, compounds A, D, L and X were found to give excellent control of crabgrass at application rates of about 1.25 pounds per acre with no damage to cotton plants. Similarly, Compounds F, M, N, O, P, Q, R, S, T, U, V and X were found to give excellent control of one or more of plant species crabgrass, barnyard grass, Johnson grass and wild oats at application rates as low as about 0.6 pounds per acre with little or no damage to one or more of desired crop plants cotton, soybeans or sugar beets.

EXAMPLE 6

In representative pre-emergence operations, seeds of various weed species are planted in seed beds and, while exposed, sprayed with compositions containing an active test ingredient. The treated seeds are then covered with a layer of soil and the test beds maintained under conditions conducive to growth for a period of about 14 days. The test compositions are prepared as set forth above in Example 4. In representative general pre-emergence operations, each of the Compounds L, M and R (as set forth in Example 4 above) gave complete control of the growth of crabgrass, Johnson grass, barnyard grass and wild oats at low, economical application rates of ¼ pound per acre without inhibiting the growth of cotton seeds. In further such operations, each of α-(bromomethyl)-3,5-diethyl-α-(2,2,2-trichloroethyl)benzenemethanol, α-(bromomethyl)-3,4-dimethyl-α-(2,2,2-trichloroethyl) benezenemethanol and α-(iodomethyl)-α-(2,2,2-trichloroethyl)benzenemethanol test ingredients and Compounds C, E, N, R, S and T of Example 5 were found to give substantial to complete control of the growth of one or more crabgrass, barnyard grass and Johnson grass seeds species at application rates of about one-half pound per acre without substantially impairing the germination and growth of cotton and soybean seeds.

In other representative pre-emergence operations, each of the α-(chloromethyl)-3,5-diethyl-α-(2,2,2-trichloroethyl)benzenemethanol, α-(bromomethyl)-4-methyl-α-(2,2,2-trichloroethyl)benzenemethanol, α-(bromomethyl)-3-chloro-4-methyl-α-(2,2,2-trichloroethyl)benzenemethanol and α-(bromoethyl)-3,5-bis(1-methylethyl)-α-(2,2,2-trichloroethyl)benzenemethanol test ingredients and Compounds A, D, G, H, I, L, M, O, P and U of Example 5 were found to give substantial to complete control of the growth of crabgrass, barnyard grass and/or Johnson grass at an application rate of about 10 pounds per acre. Several of such test ingredients were also found to be highly active against such weed species, at low application rates; moreover, several of such test ingredients were selectively active at various rates and failed to produce any significant phytotoxic effect on the germination of the seeds of one or more desired crops such as cotton, soybeans or corn.

In other such representative operations, each of the α-(bromomethyl)-α-(2,2,2-trichloroethyl)-3-(trifluoromethyl)benzenemethanol and α-(bromomethyl)-α-(2,2-dichloroethyl)benzenemethanol test ingredients and Compound F were found to give substantially complete control of the growth of crabgrass and Giant Foxtail seeds at an application rate of 1.0 pound per acre while the 4-chloro-α-(chloromethyl)-α-(2,2,2-trichloroethyl)benzenemethanol and α-(bromomethyl)-α-(2,2,2-trichloroethyl)benzyl acetate test ingredients gave substantially complete control of crabgrass, barnyard grass and wild oats at the same application rate. All of such compounds were selective to growth of one or more of desired cotton, sugar beet or soybean seeds.

Certain of the above and other active ingredients of the present invention are also active against various of the above-named plant species as well as one or more other plant species such as, for example, pigweeds, quackgrass, nutsedge and the like and also are selective to the growth of certain desired crop plants at various application rates. Moreover, certain active ingredients of the present invention wherein $n$ is 2 and each R is substituted in the 3 and 5 ring positions have uniquely demonstrated good pre- and post-emergence control of green foxtail at various low application rates in the presence of desired crops.

The reactants employed in preparing the active ingredients of the present invention are known and are either readily available or can be prepared by those skilled in the art according to known methods or analagous methods thereto.

What is claimed is:

1. A composition comprising an inert carrier and a herbicidally-effective amount of a compound of the formula:

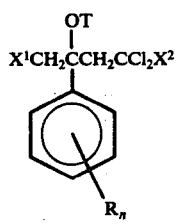

wherein x¹ represents bromo, chloro or iodo; X² represents hydrogen, chloro or methyl; n represents an integer of 0 to 3, inclusive; R is ring-substituted in the 3-, 4- or 5-positions and each R independently represents hydrogen, trifluoromethyl, alkyl of from 1 to about 3 carbon atoms, alkoxy of from 1 to about 3 carbon atoms, bromo, chloro, fluoro or nitro, and T represents hydrogen,

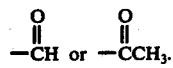

2. The composition according to claim 1 wherein n is 0.

3. The composition according to claim 1 wherein n is 1.

4. The composition according to claim 1 wherein n is 2.

5. The composition according to claim 1 wherein n is 3.

6. The composition according to claim 1 wherein T is hydrogen and X² is chloro.

7. The composition according to claim 1 wherein R is chloro or bromo and is substituted in the 3-ring position.

8. The composition according to claim 4 wherein each R is chloro or bromo and wherein said R groups are substituted in the 3-, 5-ring positions.

9. The composition according to claim 4 wherein each R is alkyl and wherein said R groups are substituted in the 3-, 5-ring positions.

10. The composition according to claim 2 wherein T is hydrogen.

11. The composition according to claim 1 wherein T is $$-\overset{O}{\underset{\|}{C}}H.$$

12. The composition according to claim 2 wherein the compound is α-(chloromethyl)-α-(2,2,2-trichloroethyl)-benzenemethanol.

13. The composition according to claim 8 wherein the compound is α-(chloromethyl)-3,5-dichloro-α-(2,2,2-trichloroethyl)benzenemethanol.

14. The composition according to claim 1 which is α-(bromomethyl)-α-(2,2,2-trichloroethyl)benzenemethanol.

15. The composition according to claim 9 which is α-(bromomethyl)-3,5-dimethyl-α-(2,2,2-trichloroethyl)-benzenemethanol.

16. The composition according to claim 7 which is α-(bromomethyl)-3-chloro-α-(2,2,2-trichloroethyl)benzenemethanol.

17. The composition according to claim 7 which is 3-chloro-α-(chloromethyl)-α-(2,2,2-trichloroethyl)benzenemethanol.

18. The composition according to claim 7 which is 3-chloro-α-(chloromethyl)-α-(2,2,2-trichloroethyl)benzenemethanol.

19. The composition according to claim 1 wherein a surface active agent is included.

20. The composition according to claim 1 together with a solid carrier.

21. The composition according to claim 1 together with a liquid carrier.

22. The method of controlling undesired plant growth which comprises applying to the locus of said plants a herbicidally-effective amount of a compound of the formula:

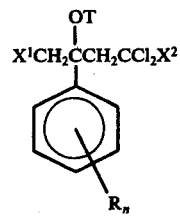

wherein X¹ represents bromo, chloro or iodo; X² represents hydrogen, chloro or methyl; n represents an integer of 0 to 3, inclusive; R is ring-substituted in the 3-, 4- or 5-positions and each R independently represents hydrogen, trifluoromethyl, alkyl of from 1 to about 3 carbon atoms, alkoxy of from 1 to about 3 carbon atoms, bromo, chloro, fluoro or nitro, and T represents hydrogen,

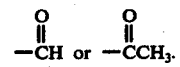

23. The method according to claim 22 wherein n is 0.
24. The method according to claim 22 wherein n is 1.
25. The method according to claim 22 wherein n is 2.
26. The method according to claim 22 wherein n is 3.
27. The method according to claim 22 wherein T is hydrogen and X is chloro.
28. The method of claim 24 wherein R is chloro or bromo and is substituted in the 3-ring position.
29. The method of claim 25 wherein each R is chloro or bromo and is substituted in the 3-, 5-ring positions.
30. The method according to claim 25 wherein each R is alkyl and is substituted in the 3-,5-ring positions.
31. The method according to claim 23 in which the compound is α-(chloromethyl)-α-(2,2,2-trichloroethyl)-benzenemethanol.
32. The method according to claim 29 in which said compound is α-(chloromethyl)-3,5-dichloro-α-(2,2,2-trichloroethyl)benzenemethanol.
33. The method of claim 23 wherein the compound is α-(bromomethyl)-α-(2,2,2-trichloroethyl)benzenemethanol.
34. The method of claim 30 wherein the compound is α-(bromomethyl)-3,5-dimethyl-α-(2,2,2-trichloroethyl)-benzenemethanol.
35. The method of claim 28 wherein the compound is α-(bromomethyl)-3-chloro-α-(2,2,2-trichloroethyl)benzenemethanol.
36. The method of claim 28 wherein the compound is 3-chloro-α-(chloromethyl)-α-(2,2,2-trichloroethyl)benzenemethanol.
37. The method of claim 28 wherein the compound is 3-bromo-α-(chloromethyl)-α-(2,2,2-trichloroethyl)benzenemethanol.

* * * * *

UNITED STATES PATENT AND TRADEMARK OFFICE
CERTIFICATE OF CORRECTION

PATENT NO. : 4,050,922

DATED : September 27, 1977

INVENTOR(S) : Lowell D. Markley

It is certified that error appears in the above-identified patent and that said Letters Patent are hereby corrected as shown below:

Column 7, line 33, should read --3,5-Dibromo-α-(bromomethyl)-α-(2,2,2-trichloroethyl)- --.

Column 7, line 40, should read --ethyl)benzenemethanol;--.

Column 7, line 47, should read --α-(Bromoethyl)-3,5-difluoro-α(2,2,2-trichloroethyl)ben- --.

Column 7, line 55, should read --α-(Bromomethyl)-5-chloro-α-(2,2-dichloropropyl)-3-tri- --.

Column 7, line 67, should read --α-(Iodomethyl)-α-(2,2-dichloropropyl)-3,5-dimethyl-4- --.

Column 11, line 50, "N." should read --N,--.

Column 12, line 6, "benezenemethanol" should read --benzenemethanol--.

Column 13, line 12, "x$^1$" should read --X$^1$--.

UNITED STATES PATENT AND TRADEMARK OFFICE
CERTIFICATE OF CORRECTION

PATENT NO. : 4,050,922

DATED : September 27, 1977

INVENTOR(S) : Lowell D. Markley

It is certified that error appears in the above-identified patent and that said Letters Patent are hereby corrected as shown below:

Column 14, line 2, Claim 18, should read
--3-bromo-α-(chloromethyl)-α-(2,2,2-trichloroethyl)ben- --.

Signed and Sealed this

Fourteenth Day of February 1978

[SEAL]

Attest:

RUTH C. MASON
Attesting Officer

LUTRELLE F. PARKER
Acting Commissioner of Patents and Trademarks